United States Patent [19]
Chaplan et al.

[11] Patent Number: 6,166,085
[45] Date of Patent: Dec. 26, 2000

[54] METHOD OF PRODUCING ANALGESIA

[75] Inventors: Sandra Reading Chaplan, San Diego, Calif.; Flemming Winther Bach, Aarhus, Denmark; Tony Lee Yaksh, San Diego, Calif.

[73] Assignee: The Regents of the University of California, Oakland, Calif.

[21] Appl. No.: 08/713,339

[22] Filed: Sep. 13, 1996

Related U.S. Application Data

[63] Continuation-in-part of application No. 08/422,377, Apr. 14, 1995.

[51] Int. Cl.$^7$ .................................................. A61K 31/52
[52] U.S. Cl. ........................ 514/626; 514/817; 424/253; 424/248.54; 424/267
[58] Field of Search ................................. 514/626, 817; 424/253, 248.54, 267

[56] References Cited

U.S. PATENT DOCUMENTS

| | | |
|---|---|---|
| 3,689,555 | 9/1972 | Schut et al. . |
| 4,001,413 | 1/1977 | Adams et al. ........................ 424/253 |
| 4,532,249 | 7/1985 | Molnar et al. . |
| 5,496,854 | 3/1996 | Keinan . |

OTHER PUBLICATIONS

Abu–Shady, H., et al., "Synthesis of some 4–aminophenol derivatives of expected pharmacodynamic activity", *Chemical Abstracts*, Abstract No. 477795 (1976) [*Egypt. J. Pharm. Sci.*, 16(3):289–96 (1976)].

*Primary Examiner*—Keith MacMillan
*Attorney, Agent, or Firm*—Fulbright & Jaworski

[57] ABSTRACT

The invention relates to methods of producing analgesia, particularly in the treatment-of-acute and persistent pain and neuropathic pain. The compound 2(ethylamino)-N-(3-hydroxy-2,6-dimethylphenyl) acetamide, or 3-hydroxymonoethylglycinexylidide (3-hydroxy MEGX), is shown to provide analgesia in settings of acute, persistent and neuropathic pain.

13 Claims, 10 Drawing Sheets

METHOD OF PRODUCING ANALGESIA

This application is a continuation-in-part of application Ser. No. 08/422,377 filed Apr. 14, 1995.

This invention was made with Government support under Grant No. DA02110, awarded by the National Institutes of Health. The Government has certain rights in this invention.

FIELD OF THE INVENTION

The Present invention relates to methods of producing analgesia, particularly in the treatment of acute and persistent pain and neuropathic pain.

BACKGROUND OF THE INVENTION

Chronic or intractable pain, such as may occur in conditions such as bone degenerative diseases and cancer, is a debilitating condition which is treated with a variety of analgesic agents, and often with opioid compounds, such as morphine. Although brain pathways governing the perception of pain are still incompletely understood, sensory afferent synaptic connections to the spinal cord, termed "nociceptive pathways," have been documented in some detail (McGeer, 1987). Analgesia, or the reduction of pain perception, can be effected by decreasing transmission along such nociceptive pathways.

Neuropathic pain is a particular type of pain that has a complex and variable etiology. It is generally a chronic condition attributable to complete or partial transection of a, nerve or trauma to a nerve plexus or soft tissue. This condition is characterized by hyperesthesia (enhanced sensitivity to a natural stimulus), hyperalgesia (abnormal sensitivity to pain), allodynia (widespread tenderness, characterized by hypersensitivity to tactile stimuli), and/or spontaneous burning pain. In humans, neuropathic pain tends to be chronic and may be debilitating.

Neuropathic pain is generally considered to be non-responsive or only partially responsive to conventional opioid analgesic regiments (Jadad, et al., 1992). Opioid compounds may also induce tolerance in patients, requiring increased dosages. At high doses, these compounds produce side effects, such as respiratory depression, which can be life threatening, and may also produce physical dependence in patients. For these reasons, alternate therapies for the management of chronic or neuropathic pain are widely sought.

Lidocaine is an well known analgesic compound with sodium channel blocking properties. It operates as a local anesthetic by inhibiting the ionic fluxes needed for conduction of impulses across neuronal membranes. several recent studies have also shown lidocaine to be useful in treatment of neuropathic and central pain. See, for example, Sotgui, et al., 1994, 1995 (neuropathic rat models); Rowbotham, et al., 1995 (postherpetic neuralgia); Fukuda, et al. 1994, Kastrup, et al., 1987, 1989; Ackerman, et al., 1991 (diabetic neuropathy); DeVulder, et al., 1993; Ellemann, et al., 1989 (cancer patients); Tanelian, et al., 1991 (acute nerve injury) and Edmondson, et al., 1993 (post stroke pain).

However, because of potentially serious side effects, which can include spinal block, respiratory arrest, and cardiac arrest, minimal dosages are recommended when lidocaine hydrochloride is administered systemically for anesthesia, and it must be administered under careful supervision (Physician's Desk Reference, 1994).

Lidocaine also has low water solubility (octanol/water partition coefficient=43 at pH 7.4). It is generally prepared as an acidic solution of the salt to promote solubility, although it is the nonionic (free base) form that permeates the nerve membrane and sheath (Tsai, et al., 1989).

It is therefore desirable to provide analgesic compounds which have low toxicity at effective dosage levels, have improved water solubility, and are effective in treatment of neuropathic pain.

SUMMARY OF THE INVENTION

The invention includes, in one aspect, a method of treating pain, including neuropathic pain. In accordance with the method, a composition comprising an effective amount of 2-(ethylamino)-N-(3-hydroxy-2,6-dimethylphenyl) acetamide, also known, and variously referred to herein, as 3-hydroxy monoethylglycinexylidide or 3-hydroxy MEGX (see structure 3 in FIG. 1), or a pharmaceutically acceptable salt thereof, in a pharmaceutically acceptable carrier, is administered to a subject in need of such treatment.

Preferably, the salt is a halide, carboxylate, sulfonate, or sulfate. Most preferably, the salt is a chloride. In one embodiment of the invention, the pharmaceutically acceptable vehicle is an aqueous carrier.

These and other objects and features of the invention will become more fully apparent when the following detailed description of the invention is read in conjunction with the accompanying drawings.

DETAILED DESCRIPTION OF THE INVENTION

I. Preparation of 3-Hydroxy Monoethylglycinexylidide

In accordance with the current invention, the lidocaine analog and metabolite 2-(ethylamino)-N-(3-hydroxy-2,6-dimethylphenyl) acetamide, also known as 3-hydroxy-N-(N-ethylglycyl)-2,6-xylidine or 3-hydroxy monoethylglycinexylidide (3-hydroxy MEGX), provides analgesia in settings of acute, persistent and neuropathic pain.

Figure 1:
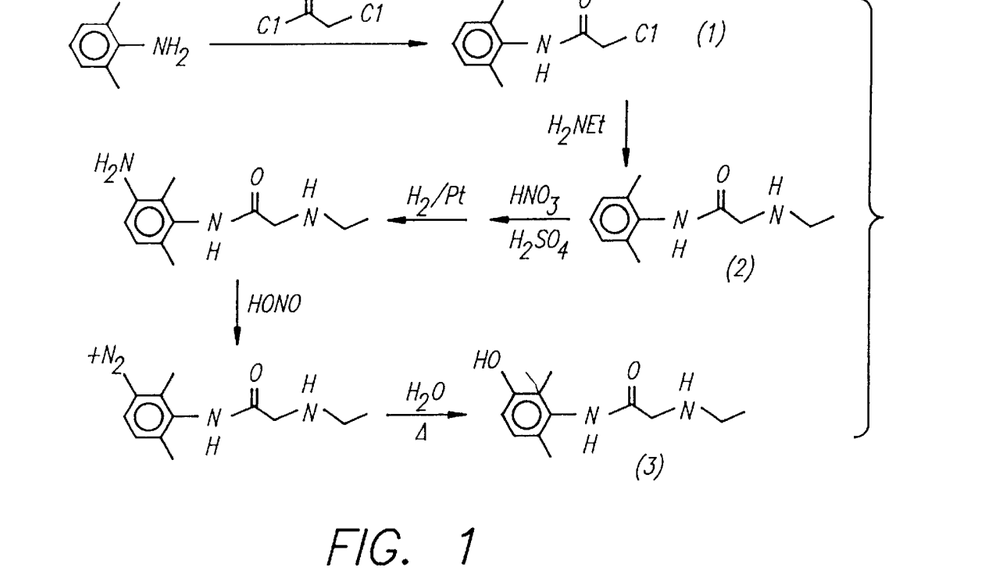
FIG. 1 shows a synthetic scheme for the preparation of 3-hydroxy MEGX.

The compound may be prepared according to methods described in, e.g., Keenaghan, et al., 1972; Nelson, et al., 1977; and Glushkov, et: al. (1992), as shown in FIG. 1. As in standard syntheses of lidocaine, 2,6-xylidine is first acylated with chloroacetyl chloride, or, alternatively, with the reaction product of chloroacetic acid with acetic anhydride (Glushkov, et al.), to give 2-chloro-N-(2,6-dimethylphenyl) acetamide (1). Reaction with ethylamine gives 2-(ethylamino)-N-(2,6-dimethylphenyl) acetamide (2). Nitration of the benzene ring, followed by diazotization and hydrolysis (Keenaghan, et al.) gives the phenol, 2-(ethylamino)-N-(3-hydroxy-2,6-dimethylphenyl) acetamide, or 3-hydroxy MEGX (3). As shown in Scheme 2 of the parent application, Ser. No. 08/422,377, diazotization and hydrolysis can also be accomplished by reaction with sodium hydroxide solution.

The compound may also be administered as a pharmaceutically acceptable salt. The anionic counterion is preferably a halide or a carboxylate-, sulfonate-, or sulfate-containing ion. More preferably, the counterion is chloride, bromide, acetate, oxalate, maleate, fumarate, methanesulfonate, or toluenesulfonate. Most preferably, the counterion is chloride.

II. Analgesic Activity

In accordance with the invention, it has been found that 3-hydroxy MEGX is effective as an analgesic agent. Analgesia in vivo is conveniently measured in one or more of a number of animal models, in which an animal's response to a given pain stimulus is measured.

A. Formalin Test

One such model, for response to an acute stimulus, is the rat formalin test. This test reflects several levels of processing of nociceptive information in the spinal cord (see Wheeler-Aceto, et al. 1990; Wheeler-Aceto, et al., 1991). Protracted sensory input generated by the noxious stimulus employed in this test (formalin in the paw) has been shown to induce an acute pain response phase (phase 1) followed by a second phase (phase 2). This second phase is thought to represent a state of facilitated processing evoked by the afferent input present during phase 1 and to involve release of at least two substances, glutamate and a, tachykinin, based on pharmacological evidence (Yamamoto and Yaksh, 1991, 1992).

In the rat formalin test, a standard dose of formalin is injected into the rat paw, and flexions of the paw are quantitated over the following 90 minute period (Example 1). A biphasic response pattern is typically observed, with numerous responses observed during the period 5 min. after injection (Phase 1) and a second phase (Phase 2) which occurs during the period about 10–60 minutes following injection. The mean number of flinches per minute is recorded as a function of time.

Figure 2A:
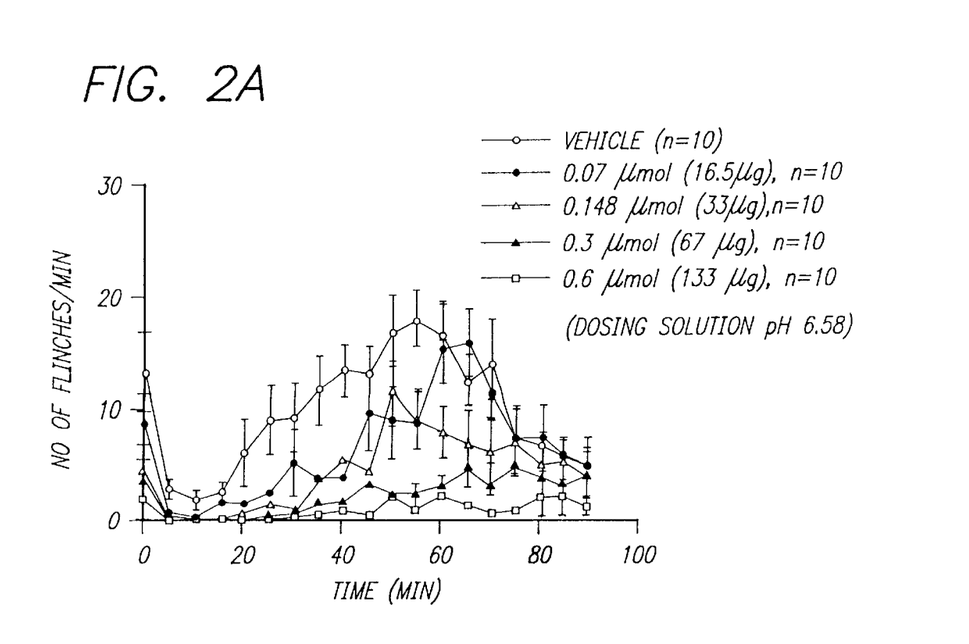
FIG. 2A shows time-effect curves for intrathecally administered 3-hydroxy MEGX at pH 6.58, showing dose-dependent blockade of acute and persistent nociceptive responses evoked by subsequent subcutaneous injection of 5% formalin into the hindpaw of Sprague-Dawley rats.
Figure 2B:
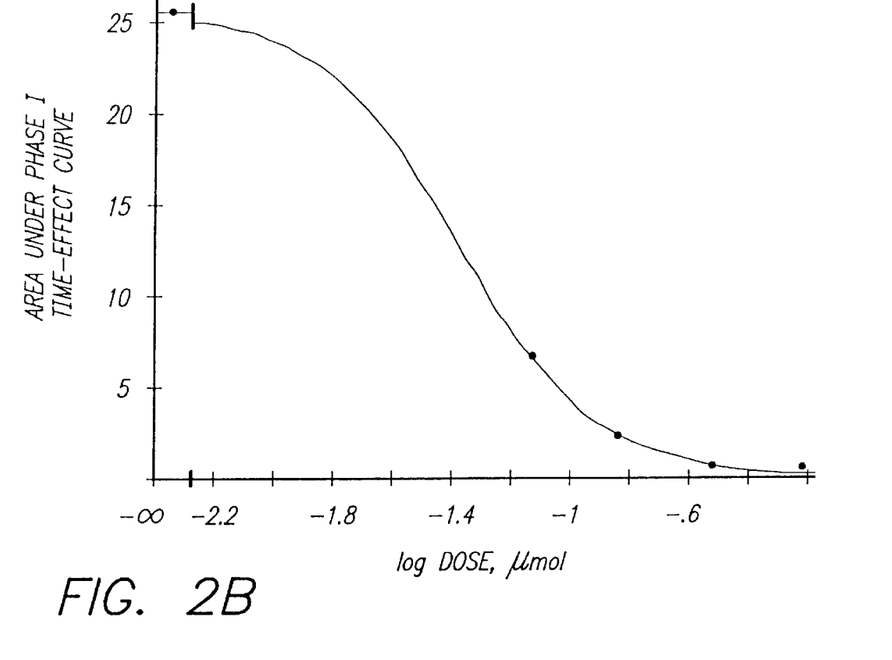
FIG. 2B is a dose-response curve derived from the data in FIG. 2A, showing the effects of 3-hydroxy MEGX at pH 6.58 on acute (Phase 1) formalin-induced nociceptive responses in Sprague-Dawley rats.
Figure 2C:
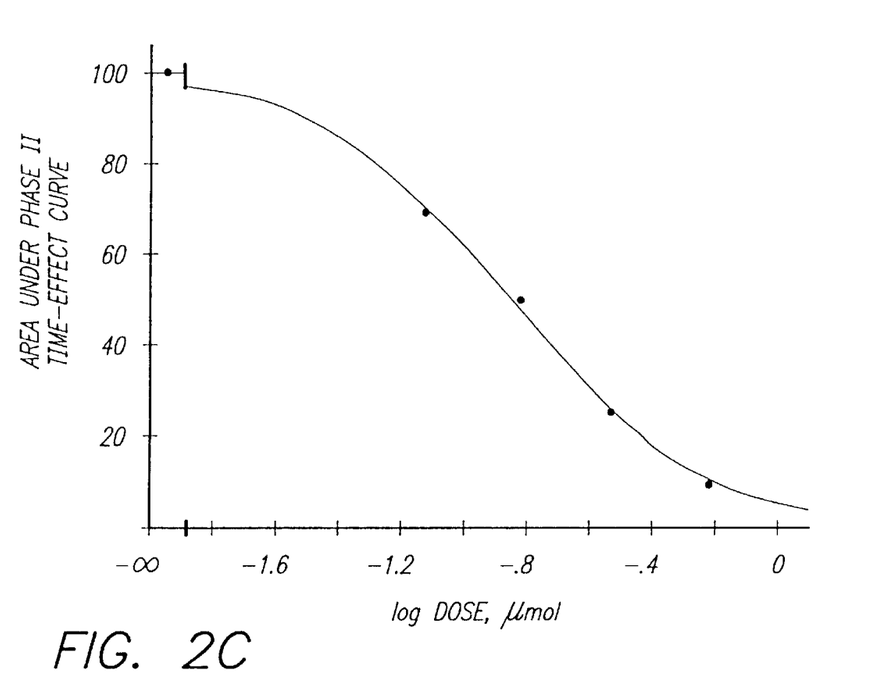
FIG. 2C is a dose-response curve derived from the data in FIG. 2A, showing the effects of 3-hydroxy MEGX at pH 6.58 on persistent (Phase 2) formalin-induced nociceptive responses in Sprague-Dawley rats.

Quantitation of responses during each phase is made by calculation of area under the curve of flinches/min., as shown in FIGS. 2B–2C.

Figure 3:
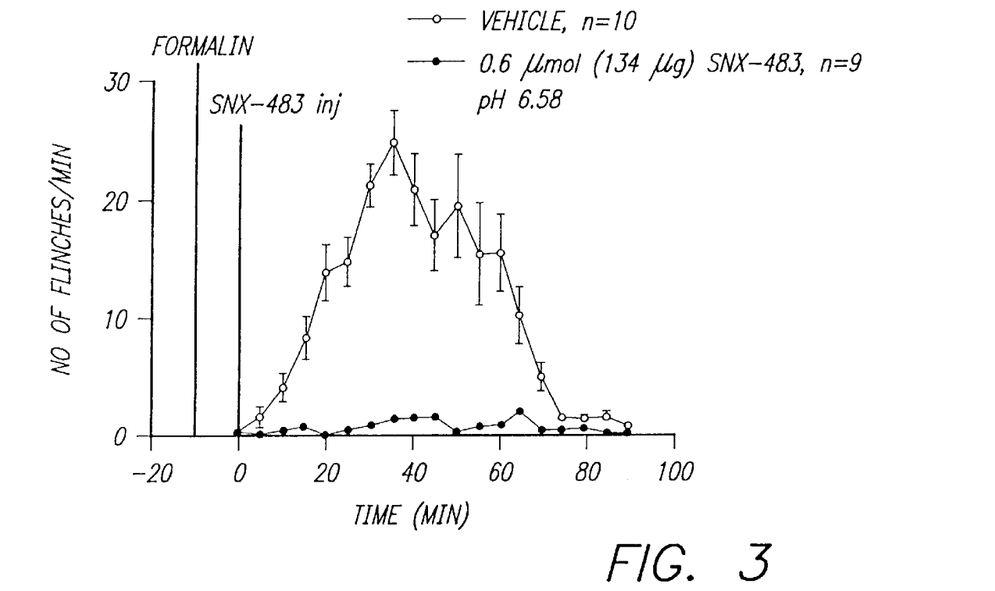
FIG. 3 shows the time-effect curve for 3-hydroxy MEGX administered by intrathecal injection after injection of 5% formalin into the hindpaw of Sprague-Dawley rats, showing blockade of persistent (Phase 2) nociceptive responses.
Figure 5A:
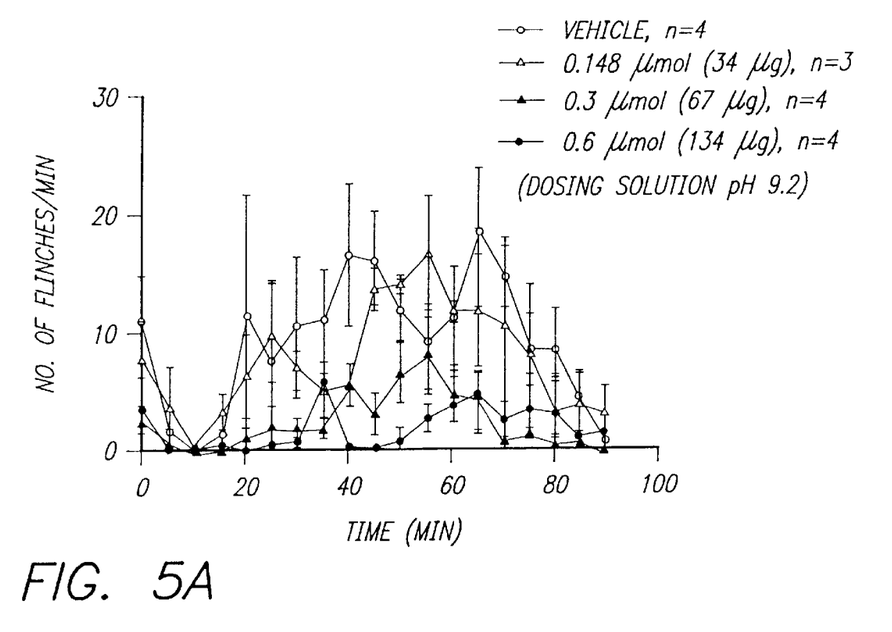
FIG. 5A shows time-effect curves for intrathecally administered 3-hydroxy MEGX at pH 9.2, showing dose-dependent blockade of acute and persistent nociceptive responses evoked by subsequent subcutaneous injection of 5% formalin into the hindpaw of Sprague-Dawley rats, as in FIG. 2A.
Figure 5B:
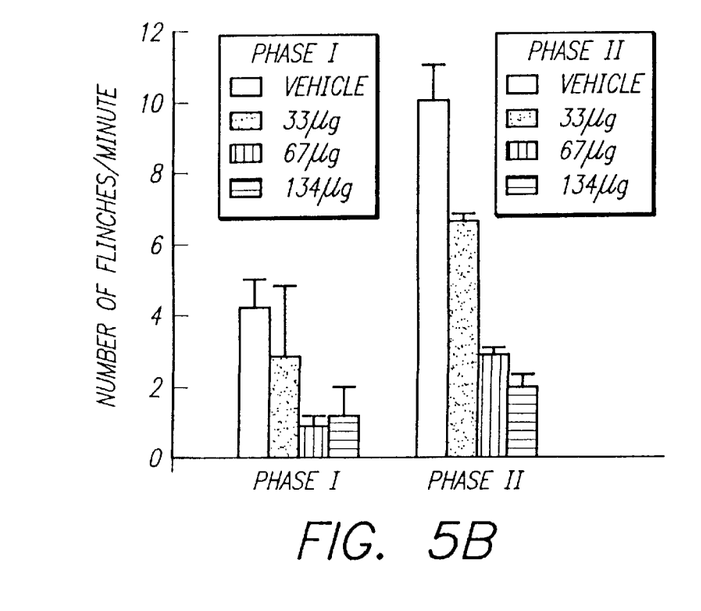
FIG. 5B illustrates dose-dependent blockade by 3-hydroxy MEGX at pH 9.2 of formalin-induced acute and tonic nociceptive responses in Sprague-Dawley rats.

FIGS. 2, 3 and 5 show results of experiments in which varying doses of 3-hydroxy MEGX designated 3-hydroxy MEGX, were tested for effects on the formalin response in rats. A 5% formalin solution was injected subcutaneously into the hindpaw of Sprague-Dawley rats. Ten minutes prior to formalin injection, 3-hydroxy MEGX was administered by bolus injection through an indwelling spinal (intrathecal) catheter terminating at the lumbar enlargement. For the results shown in FIGS. 2A–2C, dosing solutions were acidified to pH 6.58 with HCl. Injection volume was 20 μl.

FIG. 2A shows time-effect curves for blockade of acute (Phase 1, 0–9 minutes) and persistent (Phase 2, 10–90 minutes) pain by varying doses of 3-hydroxy MEGX. As can be seen from FIG. 2A, the lowest dose of SNX-433 used (16.5 μg) showed inhibition of both the Phase 1 and Phase 2 responses, with inhibition lasting up to one hour. Higher doses showed greater and longer-lived (up to 90 minutes or longer) inhibition.

FIGS. 2B and 2C show dose-response curves generated from these data by plotting the area under the time-effect curve for a given phase against dosage. $ED_{50}$ doses (doses which produced approximately 50% inhibition) were determined from the dose-response curves for Phase 1 and Phase 2 responses. For 3-hydroxy MEGX, the Phase 1 $ED_{50}$ was 9.3 μg (42 nmol), and the Phase 2 $ED_{50}$ was 29.9 μg (135 nmol).

FIGS. 5A–5B further illustrate dose-dependent blockade by 3-hydroxy MEGX of formalin-induced acute and persistent nociceptive responses in Sprague-Dawley rats, where dosing solutions of 3-hydroxy MEGX were adjusted to pH 9.2. Each histogram in FIG. 5B represents the mean (n=4 animals/group) total number of flinches observed during the indicated phase.

In the standard rat formalin test, as described above, the test substance is administered prior to formalin injection. As shown in FIG. 3, it has been found that 3-hydroxy MEGX also blocks persistent (Phase 2) nociceptive responses in the rat paw formalin test, compared to controls, when administered intrathecally after formalin injection. This observation indicates that 3-hydroxy MEGX blocks nociceptive behavior produced by preexisting facilitated states of spinal nociceptive processing.

The results shown in FIGS. 2, 3 and 5 indicate that 3-hydroxy MEGX is effective in-relieving both acute and persistent nociceptive pain, at both physiological (pH=6.58) and basic pH. Furthermore, in all of the above studies, administration of 3-hydroxy MEGX produced no overt changes in behavior.

Figure 4:
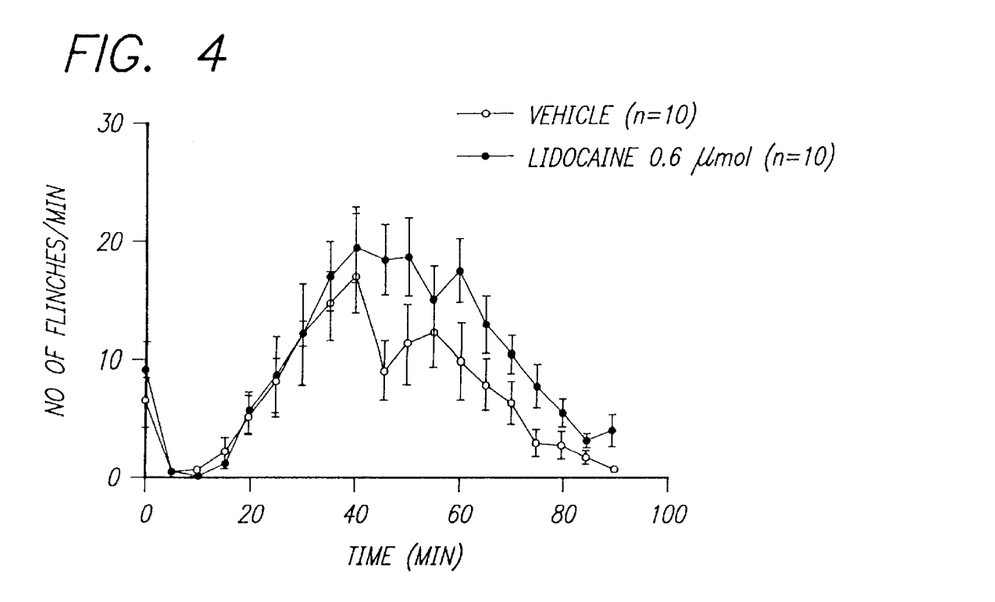
FIG. 4 shows the time-effect curve for intrathecally administered lidocaine at pH 6.58, showing the effect on formalin-induced paw flinch behavior in adult Sprague-Dawley rats.

In a separate study, similar tests were carried out using lidocaine. Dosing solutions were acidified to pH 6.58 with HCl; injection volume was 20 µl. Results are shown in FIG. 4. As can be seen from the figure, lidocaine had no effect on the formalin-induced nociceptive responses. Furthermore, administration of lidocaine in this study produced adverse side effects, in the form of transient hindlimb paresis.

B. Neuropathic Pain Models

The analgesic potency of 3-hydroxy MEGX was also tested in animal models of neuropathic or neurogenic pain. One such model resembles the human condition termed causalgia, or reflex sympathetic dystrophy (RSD), secondary to injury of a peripheral nerve. This condition is characterized by hyperesthesia (enhanced sensitivity to a natural stimulus), hyperalgesia (abnormal sensitivity to pain), allodynia (widespread tenderness, characterized by hypersensitivity to tactile stimuli), and spontaneous burning pain.

In humans, neuropathic pain tends to be chronic and may be debilitating. This type of pain is generally considered to be non-responsive or only partially responsive to conventional opioid analgesic regiments (Jadad, et al.). In accordance with the invention, 3-hydroxy MEGX is effective in providing relief of neuropathic pain, as described below.

Experiments carried out in support of the present invention were performed in a rat model of peripheral neuropathy detailed in Example 2. Briefly, in the model used, rats are subjected to a surgical procedure, described by Kim and Chung (1992), designed to reproducibly injure peripheral nerves (spinal nerves L5 and L6). These rats develop a hyperesthetic state, which can be measured using one or more paradigms known in the art. Here, allodynia was measured by stimulation of neuropathic rat hindlimb using wire hairs having graded degrees of stiffness. Analgesic compounds reverse the heightened sensitivity such animals exhibit to the stimulus.

Figure 6:
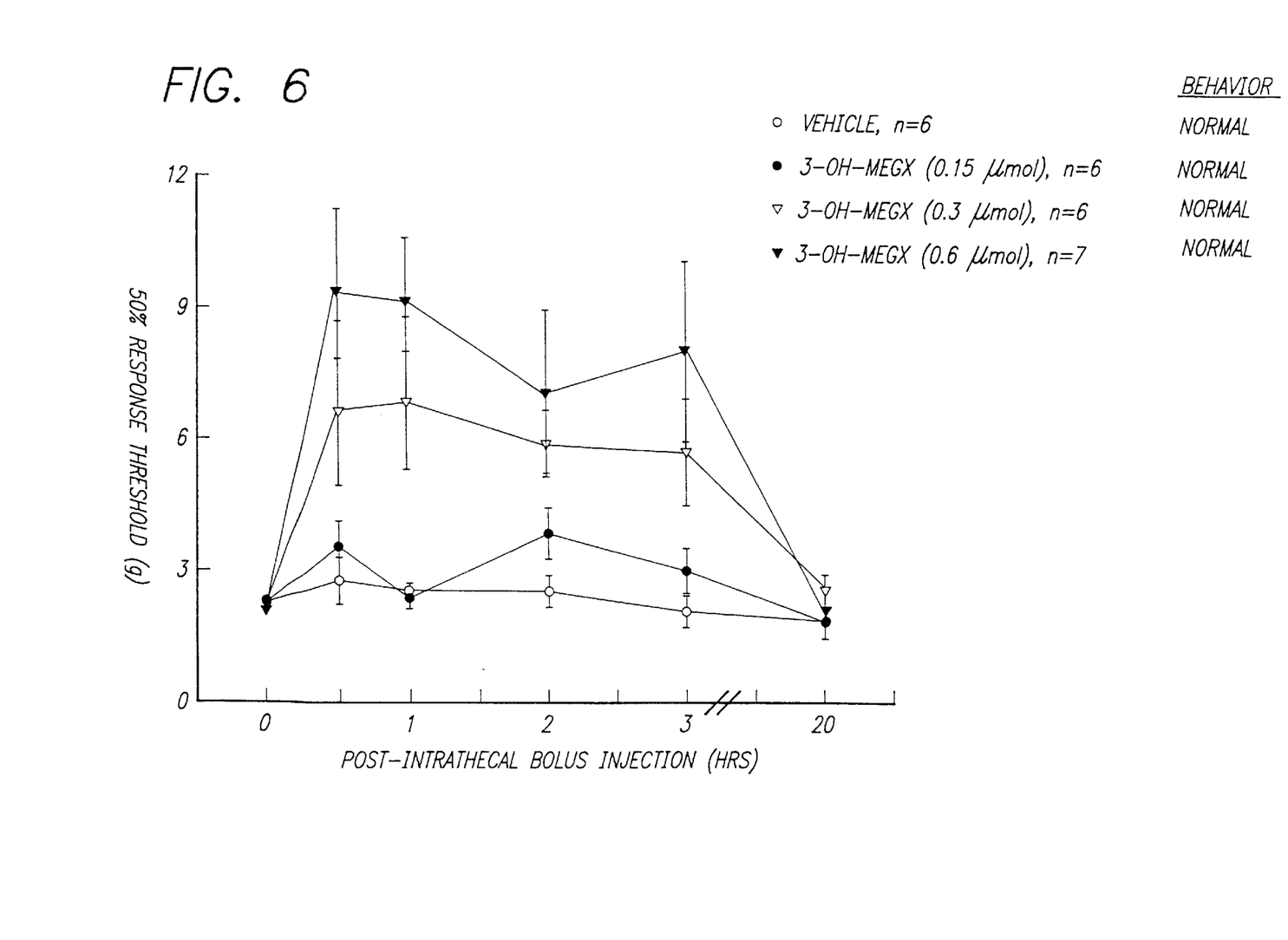
FIG. 6 shows time-effect curves showing dose dependent blockade by intrathecally administered 3-hydroxy MEGX of mechanical allodynia in Sprague-Dawley rats with a painful peripheral neuropathy produced by unilateral ligation of the L5/L6 spinal nerves distal to the dorsal root ganglia.
Figure 7:
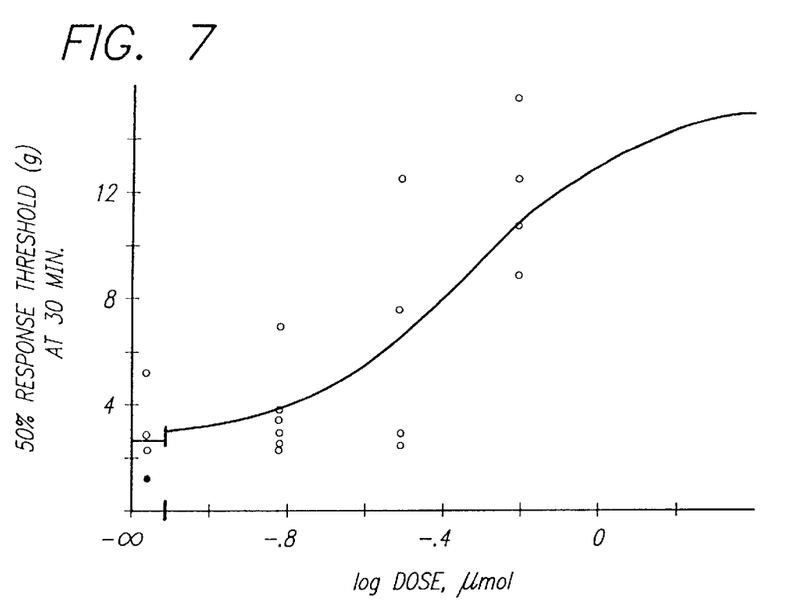
FIG. 7 shows a dose-response curve showing dose dependent blockade by 3-hydroxy MEGX of mechanical allodynia in Sprague-Dawley rats with an experimentally induced, painful peripheral neuropathy as in FIG. 6.
Figure 8:
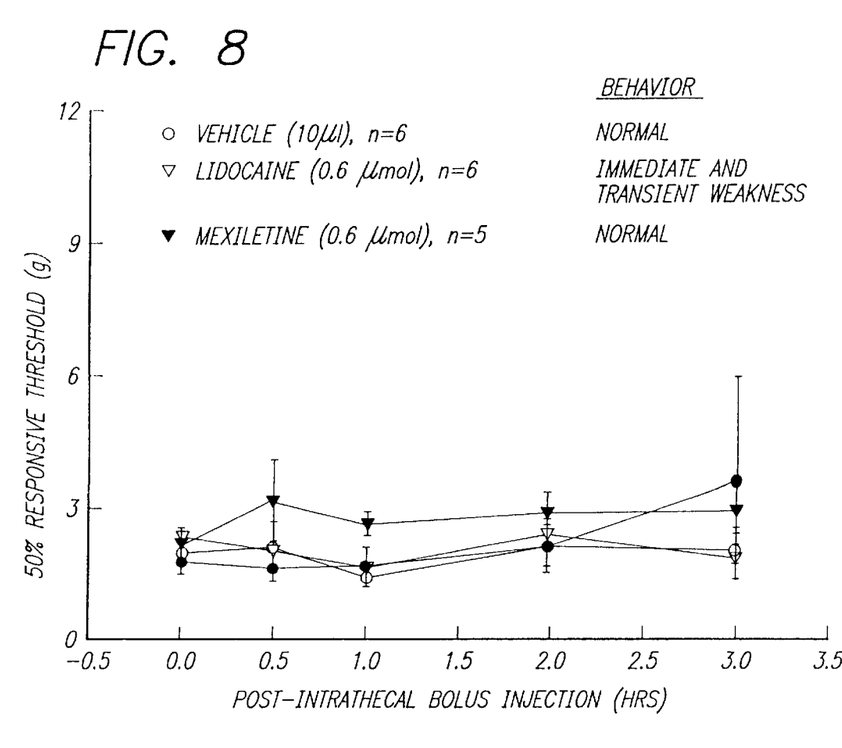
FIG. 8 illustrates mechanical allodynia thresholds in rats with an experimentally induced, painful peripheral neuropathy as in FIG. 6, after spinal (intrathecal) injections of mexiletine or lidocaine.

FIGS. 6–8 shows results in the allodynia test of animals treated with 3 hydroxy MEGX, with lidocaine, and with mexiletine, an orally available sodium channel blocker used as an anti-arrhythmia drug (FIG. 8). Test solutions at pH 6.58 were administered intrathecally as described above. Mechanical allodynia was measured by pressing nylon filaments of varying diameters against the paw. Data are expressed in terms of 50% response threshold, which is the median buckling weight required to evoke paw withdrawal; the lower the stimulus level, the more severe the allodynia.

As shown in FIG. 6, treatment of rats (n=6 animals/treatment) with varying doses of 3-hydroxy MEGX resulted in elevation of threshold response. Peak elevation of response due to drug treatment (blockade of allodynia) was observed by 30–60 minutes, and effects of a single bolus injection were long-lived, lasting in excess of 3 hours and possibly up to 20 hours. As can be seen in FIG. 6, dosages of 0.3 µmol and 0.6 µmol 3-hydroxy MEGX showed significant analgesic effects, with no observable adverse side effects.

FIG. 7 shows the dose-response curve derived from the data shown in FIG. 6. Allodynia thresholds measured 30 minutes after injection were plotted against dosage. Each point represents a value for a single animal.

In separate studies, similar tests were carried out using lidocaine and mexiletine, as described above. Dosages of 0.6 µmol were used. As shown in FIG. 8, these dosages did not block mechanical allodynia, and adverse side effects, in the form of immediate and transient weakness, were observed for rats treated with lidocaine. In contrast, as discussed above and shown in FIG. 6, lower and equivalent doses of 3-hydroxy MEGX showed significant analgesic effects, and equivalent doses showed no adverse side effects.

These results indicate that 3-hydroxy MEGX is capable of reversing the hyperesthetic effects induced by nerve damage, as well as alleviating both acute and persistent nociceptive pain. Studies in support of the invention suggest that 3-hydroxy MEGX operates via a different mechanism than lidocaine and mexiletine.

In the course of developing the present invention, the activity of lidocaine was compared with several other sodium channel blockers and with three lidocaine metabolites on tactile allodynia as measured in an experimental model for neuropathy in rats. Intravenous bupivacaine was inactive against allodynia; this substantiates previous similar observations with regard to the lack of effect of bupivacaine on centrally facilitated nociceptive processing (Biella G et al., Brain Res 603:201–206 (1992)). Spinal sodium channel blockade likewise did not seem to be sufficient to reverse allodynia; when administered IT, lidocaine had no anti-allodynic effect after termination of motor block (Chaplan S R et al., Anesthesiology 1995). Together, these observations immediately call into question the assumption that the effects of systemically administered lidocaine are attributable to the most salient pharmacological property of lidocaine, namely sodium channel blockade. 3-hydroxy MEGX did not cause motor block at an effective anti-allodynia dose.

Lidocaine had previously been shown to be effective against allodynia by the intravenous, but not the intrathecal/regional routes (Chaplan et al. (1995), supra). In my previous application Ser. No. 08/422,377, we showed that 3-hydroxy L-Lidocaine but not MEGX was an active metabolite with regard to allodynia suppression. Pursuant to the present invention, it is shown that 3-hydroxy MEGX is an active metabolite with regard to allodynia suppression.

3-hydroxy MEGX, but not MEGX, suppressed allodynia after IT administration. MEGX was administered in excess, at a dose sufficient to cause ample drug effect as witnessed by motor blockade. 3-hydroxy MEGX was administered at one order of magnitude lower concentration and yet effectively suppressed allodynia, with no evidence of motor effects.

III. Dosages and Formulations

Generally, dosages and routes of administration of the compound will be determined according to the site of the pain and the size of the subject, according to standard pharmaceutical practices. The composition may be administered to a subject by various routes, as described in Section IV below.

Formulations containing the compounds of the invention may take the form of solid, semi-solid, lyophilized powder, or liquid dosage forms, such as, for example, tablets, pills, capsules, powders, sustained release formulations, solutions, suspensions, emulsions, suppositories, retention enemas, creams, ointments, lotions, aerosols or the like, preferably in unit dosage forms suitable for simple administration of precise dosages.

The compositions typically include a conventional pharmaceutical carrier or excipient and may additionally include other medicinal agents, carriers, adjuvants, and the like. Preferably, the composition will be about 0.5%. to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

Liquid compositions can be prepared by dissolving or dispersing the compounds (about 0.5%. to about 20%), and optional pharmaceutical adjuvants, in a carrier, such as, for example, aqueous saline, aqueous dextrose, glycerol, or ethanol, to form a solution or suspension.

For use in oral liquid preparation, the composition may be prepared as a solution, suspension, emulsion, or syrup, being supplied either in liquid form or a dried form suitable for hydration in water or normal saline.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically usually used in the manufacture of medical preparations.

An injectable composition for parenteral administration will typically contain 3-hydroxy MEGX or an acceptable salt in a suitable IV solution, such as sterile physiological salt solution. The composition may also formulated as a suspension in a lipid or phospholipid, in a liposomal suspension, or in an aqueous emulsion.

For some applications, it may be desirable to include in the 3-hydroxy MEGX composition or treatment regimen means for enhancing permeation of the active compound through meningeal membranes which may surround the damaged or target nerve. Means for enhancing trans-meningeal transport of compound are known in the art and may include encapsulating the compound in liposomal membranes, addition of a surfactant to the composition, and the like. Alternatively, or in addition, trans-meningeal transport may be facilitated by administering to the subject a hypertonic dosing solution effective to disrupt meningeal barriers, according to methods well known in the art.

Methods for preparing such dosage forms are known or will be apparent to those skilled in the art; for example, see Remington's Pharmaceutical Sciences (1980). The composition to be administered will contain a quantity of the selected compound in a pharmaceutically effective amount for effecting analgesia in a subject.

IV. Treatment Methods

The composition may be administered to a subject by a variety of known routes, e.g. orally, perineurally or parenterally, that is, by intravenous, intrathecal, subcutaneous, intraperitoneal, or intramuscular injection.

Intrathecal administration allows local administration of compound to those regions of the spinal cord, such as to dorsal horn regions at affected vertebral levels, where polysynaptic relay of pain sensation occurs. This type of local application is described in co-owned application U.S. Ser. No. 08/422,377, which is hereby incorporated by reference in its entirety. Intrathecal administration, either as a bolus dosage or as a constant infusion, delivers compound directly to the subarachnoid space containing cerebral spinal fluid (CSF). While effective, this method requires precise technical expertise to ensure delivery to the correct spot.

Delivery to spinal cord regions can also be effected by epidural injection to a region of the spinal cord exterior to the arachnoid membrane. As noted above, it may be advantageous to add to the composition means for enhancing permeation of the active compound through meningeal membranes. Such means are known in the art and include liposomal encapsulation, or addition of a surfactant or an ion-pairing agent to the peptide composition. Alternatively, or in addition, increased arachnoid membrane permeation can be effected by administering a hypertonic dosing solution effective to increase permeability of meningeal barriers.

Administration by slow infusion is particularly useful when intrathecal or epidural routes are employed. Known in the art are a number of implantable or body-mountable pumps useful in delivering compound at a regulated rate. one such pump, described in U.S. Pat. No. 4,619,652, is a body-mountable pump that can be used to deliver compound at a tonic flow rate or at periodic pulses. An injection site directly beneath the pump is provided to delivery compound to the area of need, for example, to the perineural region.

Analgesics against neuropathic pain may also be administered perineurally to affected skin regions characterized by proliferation of neurite outgrowth subsequent to nerve damage. Such perineural administration can be by topical means, either directly or with the use of a transdermal applicator. Alternatively, perineural administration may be effected by subdermal injection. Perineural delivery may also be effected by forming a cuff around the damaged nerve, preferably of a biodegradable matrix which includes the therapeutic compound. Alternatively or in addition, the therapeutic compound can be placed in close proximity to the damaged nerve by conjugating the compound to or coating the compound on a nerve splint designed for repairing damaged nerves. Examples of such nerve splints are provided by U.S. Pat. Nos. 4,534,349 and 4,920,962.

Perineural delivery may also be effected by incorporating analgesic compounds into suture materials, and using these materials to suture damaged tissues. This method is particularly useful for delivery of compound in areas where it is desirable to provide for inhibition of progression of neuropathy concomitant to tissue damage. U.S. Pat. No. 5,308,889 describes a collagen based suture material that may be suitable for use for therapeutic delivery.

One particularly useful means for delivering compound to perineural sites is transdermal delivery. This form of delivery can be effected according to methods known in the art. Generally, transdermal delivery involves the use of a transdermal "patch" which allows for slow delivery of compound to a selected skin region. Although such patches are generally used to provide systemic delivery of compound, in the context of the present invention, such site-directed delivery can be expected to provide increased concentration of compound in selected regions of neurite proliferation.

Examples of transdermal patch delivery systems are provided by U.S. Pat. No. 4,655,766 (fluid-imbibing osmotically driven system), and U.S. Pat. No. 5,004,610 (rate controlled transdermal delivery system).

For transdermal delivery, it may be desirable to include permeation enhancing substances, such as fat soluble substances (e.g., aliphatic carboxylic acids, aliphatic alcohols), or water soluble substances (e.g., alkane polyols such as ethylene glycol, 1,3-propane-diol, glycerol, propylene glycol, and the like). In addition, as described in U.S. Pat. No. 5,362,497, a "super water-absorbent resin" may be added to transdermal formulations to further enhance transdermal delivery. Examples of such resins include, but are not limited to, polyacrylates, saponified vinyl acetate-acrylic acid ester copolymers, cross-linked polyvinyl alcohol-maleic anhydride copolymers, saponified polyacrylonitrile graft polymers, starch acrylic acid graft polymers, and the like. Such formulations may be provided as occluded dressings to the region of interest, or may be provided in one or more of the transdermal patch configurations described above.

For delayed release, the analgesic compound may be included in a pharmaceutical composition for formulated for slow release, such as in microcapsules formed from biocompatible polymers or in liposomal carrier systems according to methods known in the art.

V. Therapeutic Indications

As stated above, neuropathic pain may result from a number of separate etiologies. Generally, such pain may be treated according to any of the methods of described herein. However, in many cases it will be preferable to treat the pain in a manner that addresses its specific source.

For example, when the pain is traceable to injury of a particular nerve fiber, it may be appropriate to treat such pain either by perineural application of compound to the affected nerve or by dermal application of compound to the affected region.

A discussion of specific formulations and modes of delivery can be found in foregoing Sections IV and V. This section sets forth some exemplary indications for which treatment according to the methods of the present invention may have particular therapeutic utility. The indications described below are by no means exhaustive, but are presented to illustrate some of the various therapeutic situations in which 3-hydroxy MEGX can be used in the treatment of acute, persistent or neuropathic pain.

1. Ophthalmic Indications. The eye is a heavily innervated organ. The cornea in particular is heavily innervated with C-fibers, containing an estimated 3–4000 fiber endings per $mm^2$ compared to an estimated 3–600 fiber endings per $mm^2$ of skin. Injury of the nerve fibers can lead to neuropathic pain of ophthalmic origin. For treatment with analgesic compounds such as 3-hydroxy MEGX, topical administration to the eye, or, in more severe cases, suprachoroidal administration, is preferred. Such administration may be conveniently achieved by providing a suprachoroidal implant which includes the active compound. U.S. Pat. No. 5,164,188 describes a biodegradable implant that is suitable for chronic and controlled administration of compound to the suprachoroidal space. Chronic, implanted therapeutics are also indicated after ophthalmic surgery, such as after surgery for detached retina or macular holes, where nerve damage may result.

2. Dental Indications. Delivery of analgesic compounds such as 3-hydroxy MEGX to regions of dental repair, such as endodontic repair concomitant to a root canal procedure, may be desirable as a means of alleviating neural pain or preventing progression of dental neuropathy. Here, the therapeutic compound may be included in or added to one or more of the polymer based materials or resins inserted into the root canal after removing the pulp from the region, in accordance with standard techniques known in the art.

3. Burn Injury. Burn injuries are characterized by primary hyperalgesia to thermal and mechanical stimuli. This hyperalgesia is a result of nociceptor sensitization in which neurite proliferation occurs in sensory afferent beds. In accordance with the principles discussed above, treatment of burned regions with compositions containing 3-hydroxy MEGX may provide diminished sensitization and hyperalgesia, as well as reduction of progression of the hyperalgesic response. The therapeutic composition can be applied directly to the affected regions or in a formulation that includes a protective biopolymer matrix, such as an artificial skin matrix.

4. Reflex Sympathetic-Dystrophy (RSD). RSD is thought to be due to abnormalities in the peripheral nervous system, and more particularly, to sensitization of cutaneous somatosensory afferents. Sympathetic outflow is thought to activate foci of ectopic neural hyperexcitability. Treatment of this condition and reduction of its progression may be effected by any of the various dermal (topical) or subdermal routes of delivery discussed above. Perineural delivery may also be indicated for this condition.

5. Post-Herpetic Neuralgia. Post-herpetic neuralgia is characterized, in its acute phase, by intraneural inflammation which can cause damage to primary afferent axons. This damage may result in abnormal sensitivity to cutaneous stimuli. In general, the mode of treatment of the abnormal sensitivity will depend on the location in the body of the affected nerve(s). Perineural or topical delivery of therapeutic compounds is indicated in this condition.

6. Diabetic Neuropathy. Neuropathy of primary afferent axons in long nerves is found in diabetic patients. This results in the dying-back and attempted regeneration of distal tips of primary afferent axons of these nerves. Nociceptor sensitization may ensue. Such sensitization and its progression may be treated according to one or more of the treatment methods described herein. In particular, perineural or topical application of therapeutic compound will be indicated, in accord with the location of the affected nerve and nerve beds.

7. Arthritis. Arthritis is characterized by enhanced sensation of pain via articular afferents. Generally, in treating articular afferents, therapeutic compounds will be administered perineurally, in the vicinity of the affected joint.

While the invention has been described with reference to specific methods and embodiments, it will be appreciated that various modifications may be made without departing from the invention.

RAT FORMALIN TEST FOR ANALGESIA

EXAMPLE 1

Rats (male Sprague-Dawley, 275–300 g, Harlan Industries, Indianapolis, Ind.) were implanted with lumbar intrathecal catheters under halothane anesthesia (Yaksh and Rudy, 1976). Catheters (Polyethlyene PE-10) extended from the cisterna to the rostral edge of the lumbar enlargement. Three to five days after implant, animals without motor dysfunction were tested. Drugs tested in this assay were dissolved in sterile saline (0.9% NaCl) and injected in a volume of 10 μl followed by 10 μl sterile saline to clear the catheter.

Animals were examined for the effects of drugs given in the formalin test, in which 50 μl of 5% formalin was injected on the plantar surface of the paw of a lightly anesthetized (halothane, 3%) animal. The number of spontaneous flinchings/shakings of the injected paw were counted at intervals after the injection of the formalin.

Injection of formalin alone or with vehicle (saline) resulted in a biphasic response pattern of hind paw withdrawals (see, for example, FIGS. 2A and 5A). The area under the curve of flinches/min was calculated for phase 1 (time=0–10 min) and phase 2 (10–60 min). These values were plotted against intrathecal log dose ($\mu$g) to give the results shown in FIGS. 2B and 2C.

To produce the data shown in FIG. 3, 3-hydroxy MEGX was administered after formalin injection, rather than prior to formalin injection, as described above. Dosing solutions were at pH 6.58.

In a separate study, similar tests were carried out using lidocaine. Dosing solutions were acidified to pH 6.58 with HCl; injection volume was 20 $\mu$L. Results are shown in FIG. 4.

Animals were also observed for the appearance of general motor dysfunction, as evidenced by inability to ambulate symmetrically and for any other overt signs of unusual activity.

RAT MODEL OF PERIPHERAL NEUROPATHY

EXAMPLE 2

Male Sprague-Dawley rats (200–350 gm) were prepared with chronic lumbar intrathecal catheters inserted under halothane anesthesia (Yaksh and Rudy). Animals were placed in a prone position and the left paraspinal muscles were separated from the spinous processes at the $L_4$–$S_2$ levels, as described by Kim et al. The left L5 and L6 nerve roots were exposed and tightly ligated with 6-0 surgical silk suture. The rats were allowed to recover from anesthesia. Allodynia was typically observed to occur beginning 1–2 days post surgery and continuing for as long as 45 days. For testing, animals were placed in plastic cubicles with open wire mesh bottoms. Compound dissolved in preservative-free saline solution was administered in a volume of 10 $\mu$l through the intrathecal catheter, followed by 10 $\mu$l saline to flush the catheter line. Animals were tested for allodynia at various time points after drug treatment, as described below.

To assess the threshold of a non-noxious stimulus required to produce a left hind paw withdrawal (allodynia), Von Frey hairs (ranging from 0.4–15 grams), were systematically applied to the surgically treated hind paw. Failure to evoke a response was cause to test the next stiffer hair. Evocation of a brisk withdrawal response was cause to test the next lower stimulus intensity. This paradigm was repeated according to a statistical method (Dixon, 1976) to define the 50% response threshold. Allodynia is evidenced by a threshold generally less than 4 grams (referring to the hair stimulus intensity) exhibited by all surgically treated animals.

Results of animals treated with saline or with various doses of 3-hydroxy MEGX are shown in FIGS. 6 and 7. Data in FIG. 6 are expressed in terms of 50% response threshold, which is the median buckling weight required to evoke paw withdrawal; the lower the stimulus level, the more severe the allodynia. FIG. 7 shows the dose-response curve derived from the data shown in FIG. 6. Allodynia thresholds, measured 30 minutes after injection, were plotted against dosage. Each point represents a value for a single animal.

In separate studies, similar tests were carried out using lidocaine and mexiletine. The results are shown in FIG. 8.

Animals were also observed for the appearance of general motor dysfunction, as evidenced by inability to ambulate symmetrically and for any other overt signs of unusual activity. Results are indicated in FIGS. 6 and 8.

EXAMPLE 3

Male Harlan Sprague-Dawley rats were used (100–200 g). Rats were housed 2–3 to a cage with corn cob bedding and Purina rat chow and water ad libitum, in a standard facility with a 12 h/12 h day/night cycle. After surgical procedures involving chronic indwelling catheter insertion, animals were housed singly to prevent catheter damage.

To induce neuropathy, rats were anesthetized with halothane/oxygen, and the left L5/L6 spinal nerves were exposed via a dorsal midline incision and ligated tightly with 6-0 silk suture according to the reported method )Kim S H et al., Pain 50:355–363 (1992)). Rats were allowed to recover 5–7 days before further testing or surgeries.

Intrathecal PE-10 catheters were implanted under halothane/oxygen anesthesia )Yaksh T L et al., Physiol Behav 17:1031–1036 (1976)). The catheters were 9 cm in intrathecal length and terminated near the lumbar enlargement. The rostral 3 cm of catheter was tunneled under the skin to externalize between the ears. Rats with neurologic deficits were discarded.

For intravascular access, external jugular catheters were fashioned from PE-50 tubing and inserted into an external jugular vein under halothane/oxygen anesthesia. Arterial catheters were also fashioned from PE-50 with a small bouton 1 cm from the intravascular end for suture securing; they were inserted into a carotid artery, taking care to spare the surrounding nerves. All catheters were flushed with heparinized saline (10 U/ml) and tunneled subcutaneously to emerge at the posterior base of the neck, and capped when not in use.

Monoethylglycinexylidide (MEGX) and 3-hydroxy monoethyl-glycinexylidide (3-OH MEGX) were dissolved in physiologic saline; 3-hydroxylidocaine (3-OH L) was dissolved in DMSO for intravenous administration. For intrathecal administration, 3-OH L was dissolved in a vehicle consisting of 10% DMSO, 25% propylene glycol, 25% ethanol, and 40% physiologic saline, which was found to be less irritating than DMSO.

Intravenous drugs were delivered to awake, unrestrained rats by slow infusion using a syringe pump (Harvard apparatus 22). Intrathecal drugs were delivered to awake, briefly restrained rats in a volume of 10 $\mu$l, followed by 10 $\mu$l of vehicle flush, using a calibrated tubing extension with a 30-gauge adapter fitting the implanted intrathecal catheter, attached to a geared Hamilton 100 $\mu$l glass syringe. IT drug delivery was monitored by observing the advancement of a small air bubble down the tubing.

For bupivacaine assays, samples were obtained by withdrawing and discarding approximately 0.3 cc of blood from arterial cannulae, and then withdrawing samples of approximately 0.5 cc volume. These samples were centrifuged and the plasma supernatant was frozen at −20° C. until analysis.

Bupivacaine was extracted from the thawed samples by solid-phase extraction chromatography )Chen Y et al., Therapeut Drug Monitor 14:317–321 (1992)). Sep-Pak C-18 (300 mg) cartridges were pre-conditioned with 4 ml of methanol and then 4 ml water. Internal standard (50 $\mu$l aqueous lidocaine HCl, equivalent to 2 ng/$\mu$l serum) was added to 200 $\mu$l serum and the mixture was vortexed for 30 seconds. The sample was applied to the cartridge and sequentially rinsed with 2 ml water, then 2 ml 25% methanol in water. Methanol (2×200 μl) was used to elute bupivacaine from the cartridges, and was removed by atmospheric evaporation at 45° C. Dried extracts were reconstituted in 100 μl anhydrous ethanol immediately prior to gas chromatographic (GC) analysis.

Bupivacaine was quantitated by capillary GC with nitrogen-phosphorus detection )Bjork M et al., Journal of Chromatography 533:229–234 (1990)). A Hewlett-Packard 5890 II GC was equipped with a methylsilicone gum (HP-1) capillary column (25 M×0.2 mm×0.33 μM), programmed with injector and detector temperatures of 265° C. Split injections (1.5:1) were performed with a Hewlett Packard 7673A automatic sampler, and the chromatograms were recorded and analyzed with H-P Chemstation (MSDOS) software. The helium carrier gas flow rate was 0.9 ml/min (32 psi). Hydrogen and air flow-rates in the detector were 3 and 120 ml/min, respectively. The oven temperature was programmed at 240° C. for 1 minute, raised over 1 minute to a final temperature of 270° C., and held at 270° C. for 4 minutes. Total run time was 5 minutes; lidocaine and bupivacaine eluted at 2.4 and 4.0 minutes, respectively.

Rats were placed in a plastic cage with an open wire mesh bottom and allowed to accommodate for approximately fifteen minutes. A series of 8 von Frey filaments with logarithmically incremental stiffness (0.41, 0.70, 1.20, 2.00, 3.63, 5.50, 8.50, and 15.10 g) (Stoelting, Wood Dale, Ill.) was used to determine the 50% threshold for paw withdrawal to light mechanical stimuli (PWT) as previously described (Chaplan et al J. Neurosci Methods 53:55–63, 1994). In brief, von Frey hairs were sequentially applied using an up-and-down paradigm to the left mid-plantar hindpaw with sufficient force to cause slight filament buckling. Positive responses were noted if the paw was sharply withdrawn. Previous observations had determined that normal or sham operated rats have PWT of $\geq$15 g. In cases where thresholds fell outside the range of detection, i.e., continuous positive or negative responses were observed to the limit of the range of stimuli, values of 15.00 g (normal) or 0.25 g (maximally neuropathic) were assigned respectively. Otherwise, PWT were calculated by noting the stimulus level at which the first change in behavior occurred, collecting four additional responses to the continued up-and-down oscillation of stimulus presentation around the response threshold, and interpolating the 50% response threshold. For some comparisons, raw thresholds were converted to percent of maximum possible effect (% MPE), designating pre-treatment PWT (baselines) as 0% effect, and assigning a cutoff value of 100% effect to thresholds $\geq$15 g: therefore, % MPE values near 100 indicate normal mechanical thresholds (i.e., at or near 15 g), whereas values near 0 indicate allodynia. The following equation was used to compute % MPE:

% MPE=new threshold(g)–baseline threshold(g)×100/ 15 grams— baseline threshold

Plasma drug levels and PWT were correlated using linear regression. Serially measured PWT and % MPE were compared using repeated measures ANOVA with post-hoc testing.

Intravenous infusion of bupivacaine had no effect on allodynia (15 samples from 4 rats, P=0.11, linear regression), up to plasma concentrations which caused evident toxicity as manifested by ataxia and lethargy. Higher doses resulted in seizure (mean plasma level, 7.4±0.7), N=4). FIG. 1 displays the lack of correlation between plasma bupivacaine levels and % MPE on PWT.

Figure 9:
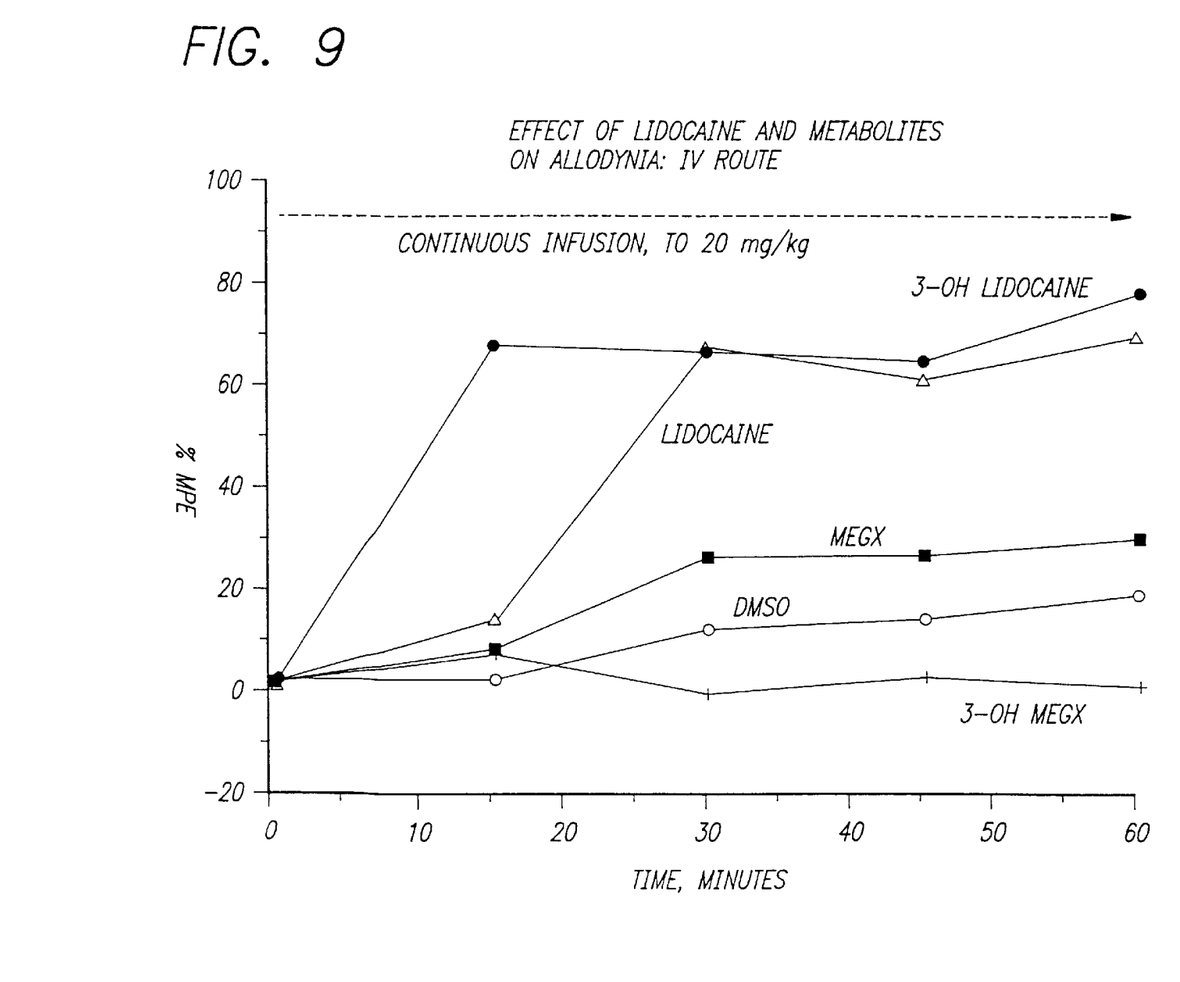
FIG. 9 illustrates the effect of constant-rate infusion of lidocaine metabolites 3-OH L (20 mg/kg total), 3-OH MEGX (20 mg/kg total), MEGX (20 mg/kg, total) Lidocaine (20 mg/kg total) and the vehicle for 3-OH, DMSO, on paw withdrawal thresholds (allodynia) (N=4 rats per group)

By IV delivery 3-OH L (20 mg/kg in DMSO) was both potent and effective at suppressing allodynia (N=4). Maximum effect on PWT was 76%±23% which was significantly different from saline (p=0.006 VS DMSO). MEGX had no effect at a dose of 20 mg/kg, infused over 60 minutes (MPE 28%±24%, P=NS vs saline). FIG. 9 shows the effect on PWT at time points after infusion of the respective metabolites/vehicles, compared with lidocaine. 3-OH MEGX did not show a significant effect in suppressing allodynia when delivered by the intravenous route (however, see below; where 3-OH MEGX is shown to have a significant effect.)

Figure 10:
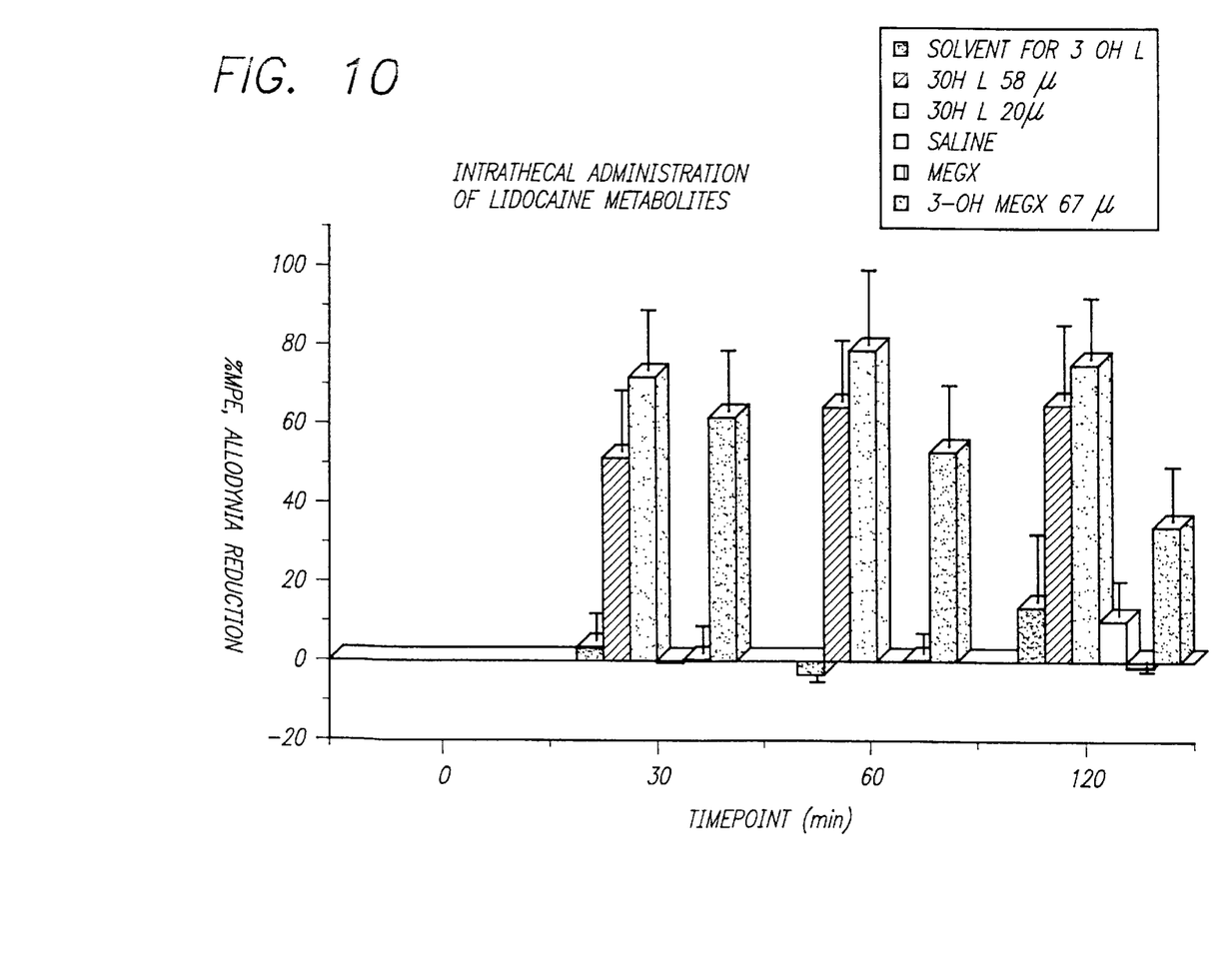
FIG. 10 depicts the effect of the intrathecal administration of limiting doses of MEGX (500 μg, limited by motor effect), 3-OH L (intrathecal injection, 58 μg, limited by solubility), 3-OH MEGX (intrathecal injection 67 μg limited by solubility), and their respective vehicles on allodynia, measured as paw withdrawal thresholds (N=6 rats per group)

The IT delivery of lidocaine, 500 μg, resulted in the acute onset of hindquarter flaccidity of approximately 10 minutes duration, during which time it was not possible to measure PWT. After recovery of motor function, allodynia thresholds remained indistinguishable from pre-drug baseline (i.e., no effect on allodynia was seen). The IT administration of 500 μg MEGX resulted in transient motor dysfunction (5–10 minutes), manifested as hindquarter weakness; after this weakness resolved, rat behavior appeared normal. MEGX showed no effect on PWT at this limiting dose, similar to observations made with lidocaine. In contrast, no motor dysfunction was seen after 3-OH L injection at the highest dose soluble in the vehicle, 58 μg. 3-OH L lidocaine at doses 20 and 58 1 g was significantly effective at suppressing allodynia: MPE was 80.2±20% and 63±16%, respectively. 3-OH MEGX also showed a significant effect at a dose of 67 μ: 63±17% MPE (P<0.0001). FIG. 10 shows the effect on PWT of IT administration of MEGX, 3-OH L (2 doses), the combination vehicle for 3-OH L, and 3-OH MEGX (1 dose) at time points after acute treatment (Chapman S R et al American Pain Society No. 95795, 1995).

EXAMPLE 4

Figure 11:
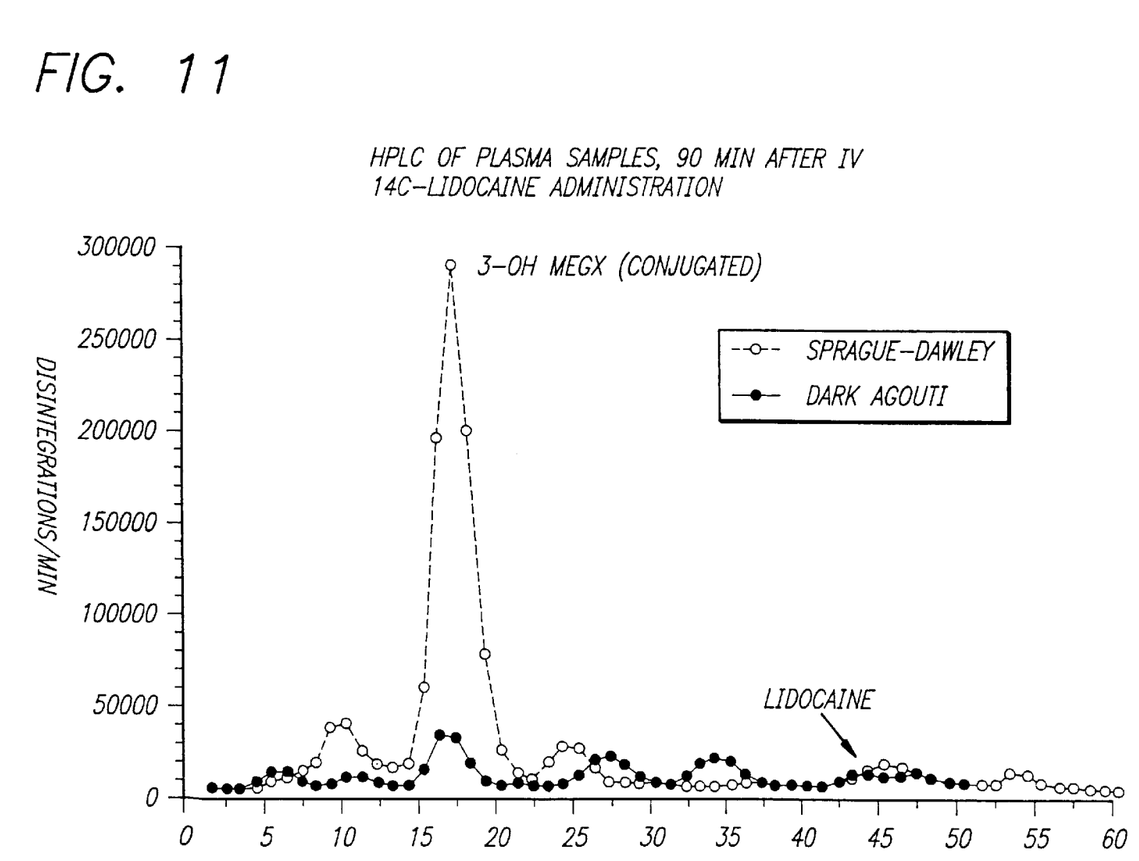
FIG. 11 shows the differing metabolic breakdown pathways in Sprague-Dawley rats (susceptible to anti-allodynia effects of Lidocaine) versus. Dark Agouti rats (not similarly susceptible), for lidocaine and 3-OH MEGX, highlighting the appearance in susceptible rats of a 3-OH metabolite.

IV administration of 14C. lidocaine (radioactive isotope) was performed in anesthetized normal Harlan Sprague-Dawley and Dark Agouti rats (N=2 each). Blood and urine samples were obtained at time points after administration and assayed for the presence of radioactive metabolites of lidocaine. Comparison of the HPLC profiles of the respective samples with mass spectroscopic confirmation, showed a marked difference in the quantities of biotransformation products between the two strains: a large peak in the elution profile of SD rats, found to consist of a glucuronidated form of 3-OH MEGX, was absent from the profile of DA rats (Rossi SR et al Therapeutic Drug Monitoring, in press). This observation serves to confirm the apparent important role of the 3-hydroxylated metabolite series in producing an anti-allodynia effect in the strain capable of demonstrating this metabolic pathway (SD). The results are shown in FIG. 11.

VI. Examination of Mechanism of Action

EXAMPLE 5

Male Harlan Sprague Dawley rats (300–350 g) were anesthetized with pentobarbital/diazepam. The sciatic nerves were sequentially and bilaterally exposed by sharp/blunt dissection from the popliteal region proximally. Electrodes were placed at the sciatic notch (stimulating), and the interossei (recording); a grounding electrode was applied remote from the field. Baseline compound action potential (CAP) (A alpha/beta) wave heights (mV) in response to stimulation 1× per minute were recorded for ten minutes to obtain a stable reference. One drug/vehicle solution was applied per nerve, at mid-nerve (mid-thigh) level, in a volume of 250 μl, and compound action potential wave height then was recorded 1× per minute for ten minutes after application. (N=4 nerves per drug.) Lidocaine was applied as a 1% solution, and metabolites were applied as 2% solutions. 3 OH L was dissolved in DMSO, and all other solutions were prepared in physiologic saline.

Figure 12:
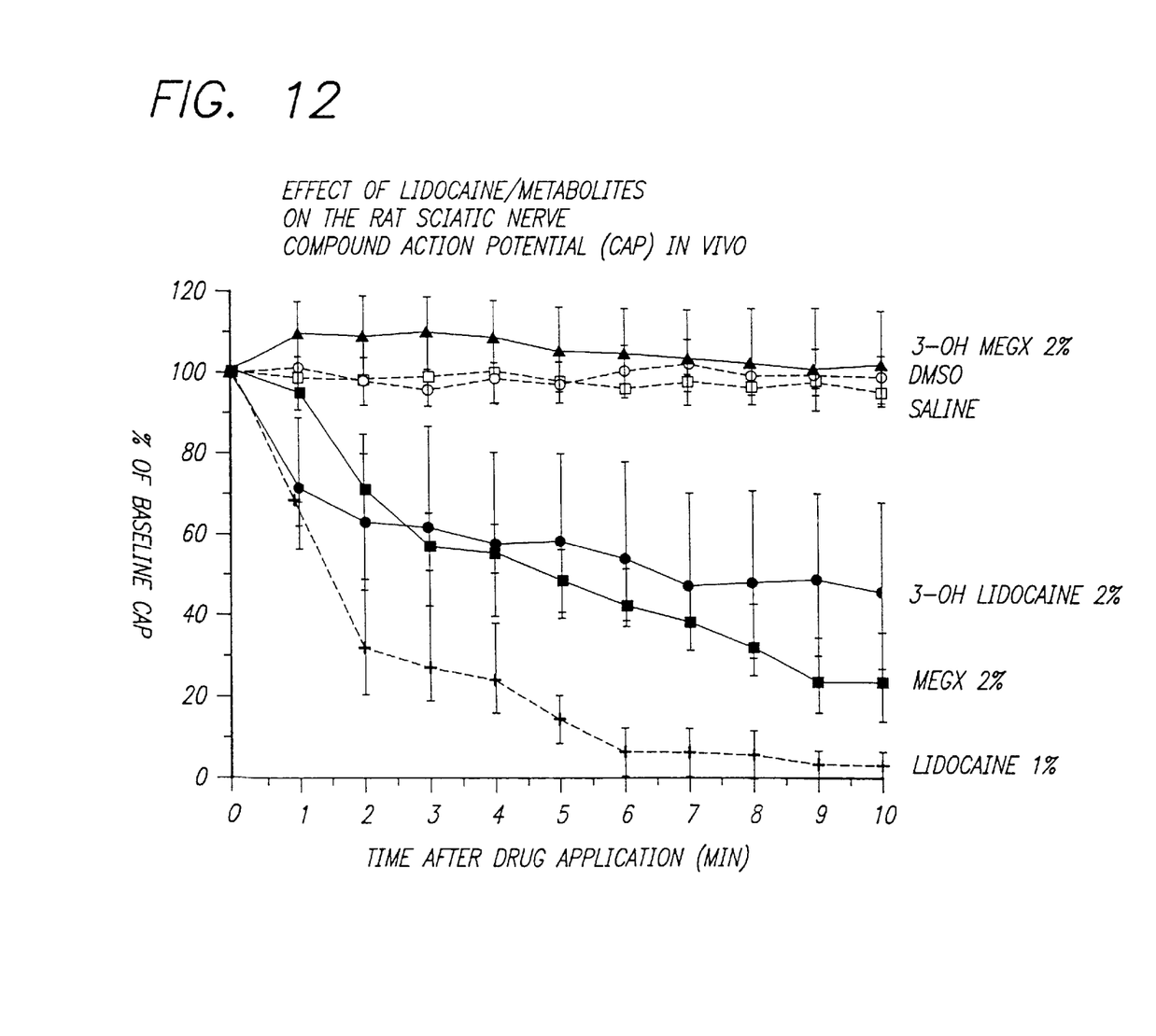
FIG. 12 shows the effect of direct application of lidocaine, 3-hydroxy lidocaine, 3-hydroxy MEGX, and MEGX (and respective vehicles saline and DMSO) as the rat sciatic nerve compound action potential in vivo, showing that 3-hydroxy lidocaine is a weaker local anesthetic than lidocaine, and 3-hydroxy MEGX appears to lack local anesthetic (sodium channel blocking) activity altogether.

FIG. 12 shows the results as changes in height of the CAP after application of drug to the exposed mid-sciatic nerve, normalized to percentage of pre-drug baseline. Lidocaine, at a dose of 2.5 mg caused rapid and complete blockade of the sciatic nerve action potential. While lidocaine 2.5 mg abolished the CAP with ten minutes, applications of metabolites at twice this dose (5 mg) had less activity (Lido>MEGS>3-OH L>>3-OH MEGX=0). Both MEGX and 3-OH L showed some activity, respectively, approximately ⅓ the potency of lidocaine (MEGX) and ¼ the potency of lidocaine (3-OH L). In this assay no blockade could be obtained with 3-hydroxy MEGX, indicating that the potency of this compound as a sodium channel blocking agent is weak or absent, and that blockade of sodium channels (as measurable with compound action potential recording) is an unlikely mechanism to account for the anti-allodynia effects seen with this agent.

It is claimed:

1. A method of treating pain, comprising administering to a subject in need of such treatment a composition comprising an effective amount of 2-(ethyl-amino)-N-(3-hydroxy-2,6-dimethylphenyl) acetamide, or a pharmaceutically acceptable salt thereof, in a pharmaceutically acceptable carrier.

2. The method of claim 1, wherein the salt is a halide, carboxylate, sulfonate, or sulfate.

3. The method of claim 2, wherein the salt is a chloride.

4. The method of claim 1, wherein the vehicle is an aqueous carrier.

5. The method of claim 1, for treatment of neuropathic pain.

6. The method of claim 1, for treatment of nociceptive pain.

7. The method of claim 1, wherein the composition is administered parenterally, orally and perineurally.

8. The method of claim 7, wherein the composition is administered subcutaneously, intraperitoneally, intravenously, intramuscularly and intrathecally.

9. The method of claim 1, wherein the composition further comprises pharmaceutical excipients selected from the group consisting of mannitol, lactose, starch, magnesium stearate, sodium saccharine, talcum, cellulose, glucose, gelatin, sucrose, magnesium carbonate and the like.

10. The method of claim 1, wherein the composition further comprises non-toxic auxiliary substances selected from the group consisting of wetting agents, emulsifying agents and buffers.

11. The method of claim 1, wherein the composition is in the form selected from the group consisting of solid, semi-solid, lyophilized powder and liquid dosage.

12. The method of claim 1, wherein the composition is a tablet, pill, capsule, powder, sustained release formulation, solution, suspension, emulsion, suppositories, retention enema, cream, ointment, lotion or aerosol.

13. The method of claim 12, wherein the composition is a tablet comprising an excipient, a binder, a filler and a disintegrator.

* * * * *